United States Patent
Beerstecher et al.

(10) Patent No.: US 6,485,304 B2
(45) Date of Patent: Nov. 26, 2002

(54) DENTAL ABRASIVE BLASTING OR JET APPARATUS

(75) Inventors: Lutz Beerstecher, Borex (CH); Jörg Wittmann, Darmstadt (DE)

(73) Assignee: Ferton Holding S.A. (CH)

(*) Notice: Subject to any disclaimer, the term of this patent is extended or adjusted under 35 U.S.C. 154(b) by 0 days.

(21) Appl. No.: 09/867,234

(22) Filed: May 29, 2001

(65) Prior Publication Data

US 2002/0004188 A1 Jan. 10, 2002

(30) Foreign Application Priority Data

May 30, 2000 (DE) .......................... 100 26 718

(51) Int. Cl.⁷ ................................................ A61C 3/02
(52) U.S. Cl. ....................................................... 433/88
(58) Field of Search .............................. 433/80, 88, 82, 433/87

(56) References Cited

U.S. PATENT DOCUMENTS

| | | | | |
|---|---|---|---|---|
| 4,482,322 A | * | 11/1984 | Hain et al. | 433/88 |
| 4,492,575 A | | 1/1985 | Mabille | 433/88 |
| 4,830,210 A | | 5/1989 | Mabille | 215/309 |
| 5,186,625 A | * | 2/1993 | Bailey | 433/88 |
| 5,312,251 A | * | 5/1994 | Jackson | 433/88 |
| 6,093,021 A | * | 7/2000 | Rainey | 433/88 |

FOREIGN PATENT DOCUMENTS

| | | |
|---|---|---|
| DE | 69002999 | 4/1994 |
| DE | 69415777 | 7/1999 |
| EP | 0268948 | 1/1992 |
| FR | 2567747 | 1/1986 |
| FR | 2575062 | 6/1986 |

\* cited by examiner

*Primary Examiner*—Cary E. O'Connor
(74) *Attorney, Agent, or Firm*—Ostrolenk, Faber, Gerb & Soffen, LLP

(57) ABSTRACT

A dental abrasive blasting or jet apparatus is provided with an interconnected handpiece having a nozzle arrangement which is supplied with a dental powder as stored in a powder reservoir and delivered under pressure by a gaseous carrier medium via a powder supply line together with a fluid that is supplied via a separate fluid supply line. The apparatus is provided with a separate fluid receptacle or bottle which is filled with a flushing or rinsing liquid for being selectively supplied to the nozzle arrangement of the handpiece via a branch line having a change-over directional valve downstream of a suction pump for supplying the flushing or rinsing liquid to the portion of the fluid supply line that is directly connected with the handpiece.

15 Claims, 1 Drawing Sheet

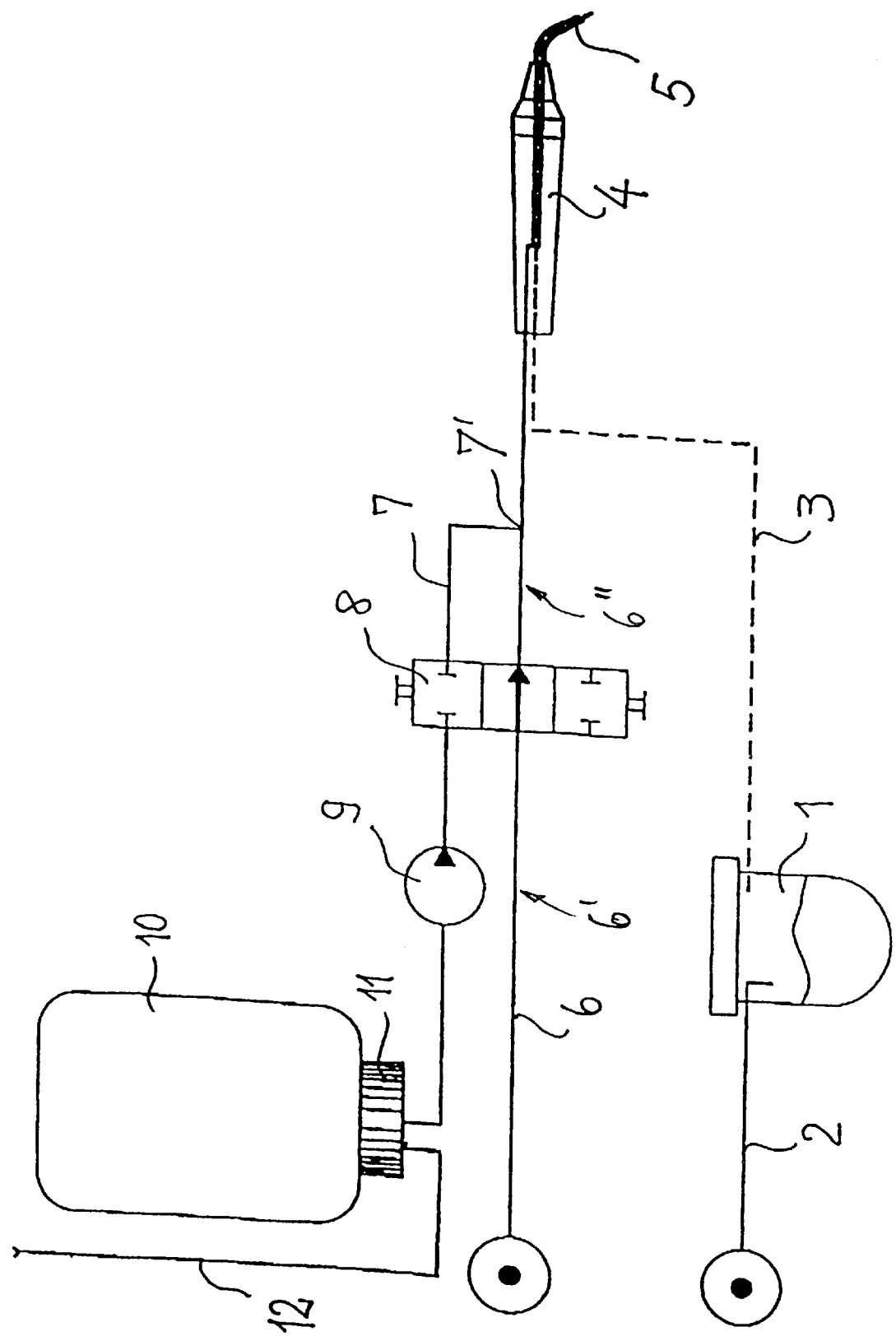

DENTAL ABRASIVE BLASTING OR JET APPARATUS

FIELD OF THE INVENTION

The present invention relates to a dental abrasive blasting or jet apparatus of the kind comprising a powder reservoir for storing a dental powder which in common with a gaseous carrier medium is supplied to a nozzle arrangement of a handpiece together with a fluid via two separate supply lines leading to the handpiece which is operatively connected with the apparatus.

BACKGROUND OF THE INVENTION

A prior art dental abrasive blasting or jet apparatus of the kind as herein referred is described in U.S. Pat. No. 4,492,575. The powder which is used with such an apparatus for prophylactic measures is stored in a receptacle inside of a casing of the apparatus. The receptacle is interconnected with a supply line for compressed air which takes up the dental powder that is stored in this receptacle for being transported as a mixture with air to a nozzle arrangement of an interconnected handpiece. The nozzle arrangement is further interconnected with a fluid supply line which supplies normal tap water to the handpiece accordingly in common with the powder and air mixture. The supply line for compressed air is provided upstream of the powder receptacle with a junction for a branch line. The branch line leads to a pinch valve which is arranged for squeezing of powder supply line to thereby interrupt a supply of the powder and air mixture to the nozzle arrangement of the handpiece. The air feeding line of this pinch valve is controlled by a solenoid control valve as arranged in the branch line. A further solenoid control valve is arranged upstream of a junction of the branch line. The two control valves are controlled such that when the air supply to the powder receptacle is interrupted the air supply to the pinch valve will then as well be interrupted for squeezing the powder supply line leading to the nozzle arrangement of the handpiece.

The U.S. Pat. No. 4,830,210 describes a closure means for a fluid receptacle or bottle which may be screw-connected with a fitting on the exterior of the casing of a dental apparatus. The receptacle or bottle is therefore exchangeably mounted on the apparatus by such a combination of a closure means and a fitting.

The European Patent EP 0 395 557 B1 discloses a dental abrasive blasting or jet apparatus which is designed as an autonomous unit by its accommodation in a case. The case also accommodates a compressor for supplying compressed air via a three-way-valve alternatively to two bottles which are filled with a dental powder and a fluid, respectively. Depending on the switch or control position of the three-way-valve either a powder and air mixture in common with the fluid or simply the fluid may be supplied via two separate supply lines to an interconnected jet arrangement of a handpiece. As fluid with which the one bottle is filled it is suggested to use either tap or distilled water or to alternatively use an aqueous solution of an antiseptic or a medicinal component.

SUMMARY OF THE INVENTION

An object of the present invention is to provide a dental abrasive blasting or jet apparatus which in the field of dental treatment will allow a broader application of the apparatus by making use not only of normal tap water but alternatively also of other fluids.

The present invention accordingly provides a dental abrasive blasting or jet apparatus which is characterised by the features as outlined in the claims.

A dental abrasive blasting or jet apparatus in accordance with the present invention therefore provides a rather simple measure as to how a dental apparatus of the kind referred may be either used with normal tap water for a powder blasting of dental surfaces in order to remove plaque and discolorations, for polishing and cleaning or purifying tooth surfaces or in general for a prophylaxis treatment of tooth surfaces. The apparatus according to the present invention may instead alternatively also be used for a blasting of different fluids against the tooth surfaces.

By the provision of an exchangeable arrangement of a separate fluid receptacle or bottle on the exterior of the apparatus there namely could be used demineralised water as a flushing or rinsing liquid alternatively to the use of a prophylactic flushing or rinsing liquid with which a different receptacle or bottle is filled whereby the liquid may comprise antimicrobiological or bacteriostatic additives that contribute to a remineralisation of teeth when added with an amount acting non-toxic on the human organism. Such additives could be selected from variable groups of chemical components as well as vegetable extracts etc. whereby all of such different flushing or rinsing liquids will be stored in separate bottles having all a closure means on a refillable bottle opening which is designed for a screw connection with the same fitting on the exterior of the apparatus.

Other objects, features and advantages of the present invention will become apparent from reading the following description of a preferred embodiment of a dental apparatus according to the present invention.

BRIEF DESCRIPTION OF THE DRAWING

The invention will now be described by way of example, with reference to the accompanying drawing which represents a diagrammatic view of the apparatus according to the present invention.

A dental abrasive blasting or jet apparatus according to the present invention is basically designed in the same manner as the dental apparatus according to the U.S. Pat. No. 4,492,575 to which reference may therefore be made for further details of the following description.

For using the apparatus in the same manner as the known apparatus as described in more detail in the before mentioned document the apparatus according to the present invention is as well provided with a receptacle 1 which as a powder reservoir is filled with a dental powder such as sodiumbicarbonate. The dental powder is supplied by means of compressed air as supplied via an interconnected supply line 2 to a powder supply line 3 of a handpiece 4 which has a jet arrangement 5 on a tip portion of the handpiece. The jet arrangement 5 of the handpiece 4 is also connected to a separate fluid supply line 6 for being supplied with normal tapwater which therefore in common with the powder and air mixture will be delivered via the jet arrangement 5 during a dental treatment. The handpiece 4 will thereby be directed with the jet arrangement on its tip portion towards the tooth surfaces for removal of plaque and discolorations or simply for polishing or cleaning the tooth surfaces by the powder blast or jet whereby the tapwater only serves the purpose of preventing any uncontrolled splashing of the powder during dental treatment and to purge off at the same time the powder particles which will remain in the mouth of the patient.

The powder which is stored in the receptacle 1 could alternatively also comprise aluminium oxide or dolomite if it should be intended to use the handpiece also for less careful cutting operations or for the removal of more persistent plaque. The dental powder could as well comprise certain additives for securing for example a caries inhibiting effect.

In accordance with the present invention the fluid supply line 6 is provided with a branch line 7 having a change-over directional valve 8 that is arranged upstream of its junction 7' by which the branch line 7 is connected with the fluid supply line. The directional valve 8 which would be solenoid controlled is arranged for interrupting the fluid supply line 6 with its portion 6' upsteam of the valve so that with its respective control position the branch line 7 will then be connected at the junction 7' with that portion 6" which downstream of the directional valve 8 directly leads to the jet arrangement 5 of the handpiece.

The branch line 7 is provided with a suction pump 9 upstream of the directional valve 8. This suction pump 9 is connected via the branch line 7 with a separate fluid receptacle or bottle 10 which is filled with a flushing or rinsing fluid for being separately supplied to the handpiece. As connecting means for connecting the branch line 7 with this separate fluid receptacle or bottle 10 the same may be provided with a closure means 11 for example of the kind as disclosed in the document EP-A-0 268 948 B1. When being provided with such a closure means it will be possible to arrange any separate fluid receptacle or bottle 10 in an exchangeable manner on the exterior of the apparatus the casing of which would then be provided with a complementary fitting (not shown) for allowing a simple screw connection. The closure means 11 should suitable also comprise an interconnected ventilating duct 12 connected t a ventilating valve (not shown) as integrated with the closure means.

The suction pump 9 is provided for sucking-off a flushing or rinsing liquid with which the fluid receptacle or bottle 10 would be filled. This flushing or rinsing liquid would therefore be supplied via the branch line 7 to the nozzle arrangement 5 of the handpiece 4 as soon as the directional valve 8 has been adjusted to its change-over position in which only the downstream portion 6" of the fluid supply line 6 will be connected with the jet arrangement 5 of the handpiece whereas the upstream portion 6' of line 6 will then be interrupted.

The flushing or rinsing liquid which will be stored in the fluid receptacle or bottle 10 would preferably be demineralised water which subsequent to a treatment with the dental powder as stored in the receptacle 1 would then be sprayed against the tooth surfaces for final cleaning purposes.

The flushing or rinsing liquid could also be a prophylactic flushing liquid containing antimicrobiological or bacteriostatic additives that will contribute to a demineralisation of the teeth when added with an amount acting non-toxic on the human organism. Such a specific flushing or rinsing liquid could as well be a flush suspension of a dental powder which contains such specific additives.

As additives which may be used for the mixing with a base powder as alternatively also available in common with a carrier substance there could be used additives from the group of the quartenary ammonium compounds, such as acetylpyridinium chloride and benzalconium chloride.

Such additives could be also selected alternatively and/or additionally from the group comprising the salts of bisguanidine, such as chlorohexidine and its salts, bispyridine, such as octenidinehydrochloride, and the specific amine salts, namely octapinol and delmopinol.

The additives could as well be selected alternatively and/or additionally from the group comprising vegetable extracts, such as camomile, sage, myrrh, ratanhia, clove, sanguinarine, fennel, mint, thyme, menthol and allantoine.

Further additives acting at least bacteriostatically would also be the group of compounds setting free oxygen and comprising peroxides, percarbonates, perborates, percarboamides, peroxomonosulfates and peroxodisulfates. Also metallic iones, such as iones of strontium and tin, and the iones of transition metals, such as copper and zinc could as well be used as more suitable additives. Also useable will be the group comprising phenoles and polyphenoles. Finally also certain flavouring agents could as well be added.

We claim:

1. A dental abrasive blasting or jet apparatus, comprising:
   a powder reservoir for storing a dental powder which in common with a gaseous carrier medium is supplied via a powder supply line to a nozzle arrangement of a handpiece together with a fluid which is supplied via a separate fluid supply line, the handpiece being operatively connected with the apparatus;
   a separate fluid receptacle or bottle which is exchangeably arranged on the exterior of the apparatus for storing a flushing or rinsing fluid which is provided for being selectively supplied to the nozzle arrangement of the handpiece separately from or in common with a supply of the mixture of the dental powder and the gaseous carrier medium;
   a branch line of said fluid supply line which is adapted for being connected to said separate fluid receptacle or bottle via a change-over directional valve which is adapted for being selectively switched to a control position in which the flushing or rinsing fluid is supplied to the jet or nozzle arrangement of the handpiece via a junction at a position downstream of said change-over directional valve at which said branch line further extends to a portion of said fluid supply line which terminates in said nozzle arrangement of the handpiece; and
   a suction pump which is arranged in said branch line at a position upstream of said change-over directional valve, the suction pump being switched-on when said change-over directional valve is adjusted to said control position so that the flushing or rinsing fluid will be sucked-off from said separate fluid receptacle or bottle for being supplied to said nozzle arrangement of the handpiece via said interconnected portion of the fluid supply line downstream of said change-over directional valve which then will interrupt said upstream portion of the fluid supply line.

2. The dental abrasive blasting or jet apparatus according to claim 1, wherein said separate fluid receptacle or bottle comprises a closure means which is adapted for being screw-connected with a fitting on the exterior of the apparatus.

3. The dental abrasive blasting or jet apparatus according to claim 2, wherein said closure means of the separate fluid receptacle or bottle comprises an interconnected ventilating duct.

4. The dental abrasive blasting or jet apparatus according to claim 3, wherein said separate fluid receptacle or bottle is filled with a suspension of a dental powder containing antimicrobial or bacteriostatic additives that contribute to a remineralisation of the teeth when added with an amount acting non-toxing on the human organism.

5. The dental abrasive or blasting jet apparatus according to claim 4, wherein said suspension is formed with sodiumbicarbonate or with hydroxylapatite as a base powder.

6. The dental abrasive blasting or jet apparatus according to claim 2, wherein said separate fluid receptacle or bottle is filled with a suspension of a dental powder containing antimicrobial or bacteriostatic additives that contribute to a remineralisation of the teeth when added with an amount acting non-toxing on the human organism.

7. The dental abrasive or blasting jet apparatus according to claim 6, wherein said suspension is formed with sodiumbicarbonate or with hydroxylapatite as a base powder.

8. The dental abrasive blasting or jet apparatus according to claim 1, wherein said separate fluid receptacle or bottle is filled with water, in particular with demineralised water.

9. The dental abrasive blasting or jet apparatus according to claim 8, wherein said separate fluid receptacle or bottle is filled with a suspension of a dental powder containing antimicrobial or bacteriostatic additives that contribute to a remineralisation of the teeth when added with an amount acting non-toxing on the human organism.

10. The dental abrasive or blasting jet apparatus according to claim 9, wherein said suspension is formed with sodiumbicarbonate or with hydroxylapatite as a base powder.

11. The dental abrasive blasting or jet apparatus according to claim 1, wherein said separate fluid receptacle or bottle is filled with a prophylactic flushing or rinsing liquid containing antimicrobiological or bacteriostatic additives that contribute to a demineralisation of the teeth when added with an amount acting non-toxic on the human organism, such additives being selected from the group of the quartenary amonioum compounds; and/or from the group comprising the salts of bisquanidine, such as chlorohexidine and its salts, bispyridine, such as octenidinehydrochloride, and the specific amine salts, namely octapinol and delmopinol; and/or from the group comprising vegetable extracts, such as camomile, sage, myrrh, ratanhia, clove, sanguinarine, fenel, mint, thyme, menthol and allantoine;

from the group of metallic iones, such as iones of strontium and tin, and the iones of transition metals, such as copper and zinc;

from the group of compounds setting free oxygen and comprising peroxides, percarbonates, perborates, percarboamides, peroxomonosufates and peroxidisulfates;

from the group of the phenoles and polyphenoles, such as thymol and triclosan.

12. The dental abrasive blasting or jet apparatus according to claim 11, wherein the prophylactic flushing or rinsing liquid contains 0.01 to 5.0 percent by weight chlorohexidine and 0.01 to 5.0 percent by weight amine fluoride.

13. The dental abrasive blasting or jet apparatus according to claim 11, wherein the prophylactic flushing or rinsing liquid contains 0.01 to 3.0 percent by weight sodium chloride, 0.01 to 2.5 percent by weight potassium sulfate, 0.01 to 5.0 percent by weight sodiumnitrate and 0.01 to 5.0 percent by weight sodiumbicarbonate as mixed with essential oils and vegetable extracts.

14. The dental abrasive blasting or jet apparatus according to claim 1, wherein said separate fluid receptacle or bottle is filled with a suspension of a dental powder containing antimicrobial or bacteriostatic additives that contribute to a remineralisation of the teeth when added with an amount acting non-toxing on the human organism.

15. The dental abrasive or blasting jet apparatus according to claim 14, wherein said suspension is formed with sodiumbicarbonate or with hydroxylapatite as a base powder.

* * * * *